United States Patent [19]

Ibrahim

[11] Patent Number: 5,178,140
[45] Date of Patent: Jan. 12, 1993

[54] IMPLANTABLE MEDICAL DEVICES EMPLOYING CAPACITIVE CONTROL OF HIGH VOLTAGE SWITCHES

[75] Inventor: Ibrahim H. Ibrahim, North Ryde, Australia

[73] Assignee: Telectronics Pacing Systems, Inc., Englewood, Colo.

[21] Appl. No.: 754,984

[22] Filed: Sep. 5, 1991

[51] Int. Cl.$^5$ ............................................. A61N 1/39
[52] U.S. Cl. ............................................. 128/419 D
[58] Field of Search ................................. 128/419 D

[56] References Cited

U.S. PATENT DOCUMENTS

| | | | |
|---|---|---|---|
| 4,170,740 | 10/1979 | Pernyeszi | 307/251 |
| 4,559,946 | 12/1985 | Mower | 128/419 D |
| 4,960,123 | 10/1990 | Maker | 128/419 D |
| 5,048,521 | 9/1991 | Pless et al. | 128/419 D |

OTHER PUBLICATIONS

S. L. Hurst book entitled "Custom-Specific Integrated Circuits," p. 111, published by Marcel Dekker, Inc., 270 Madison Avenue, New York, N.Y. 10016 (1985).

Primary Examiner—Kyle L. Howell
Assistant Examiner—Scott M. Getzow
Attorney, Agent, or Firm—Gottlieb, Rackman & Reisman

[57] ABSTRACT

An implantable device for treating a malfunctioning heart is disclosed. The device includes a high voltage circuit having a tank capacitor for storing therein during a charging mode of operation thereof high voltage DC electrical energy and for delivering such energy to a malfunctioning heart in the form of an electrical shock during a discharging mode of operation thereof. The device further includes a high voltage switch coupled to the high voltage circuit for switching, in the order of microseconds, the high voltage circuit between its charging and discharging modes of operation; a power supply for providing low voltage electrical energy for use in controlling the high voltage switch; a control circuit coupled between the power supply and the high voltage switch and capable of driving the high voltage switch to switch its output in the order of microseconds, for controlling the operation of the high voltage switch; and capacitors for capacitively coupling the power supply to the control circuit and electrically isolating the high voltage DC electrical energy from the power supply. The control circuit includes a common mode switch for rejecting common mode noise, and an additional switch for rapidly changing the output state of the high voltage switch.

16 Claims, 13 Drawing Sheets

IMPLANTABLE MEDICAL DEVICES EMPLOYING CAPACITIVE CONTROL OF HIGH VOLTAGE SWITCHES

TECHNICAL FIELD

This invention relates to implantable arrhythmia control systems and, more particularly, to circuits for driving high voltage metal oxide semiconductor field effect transistors (MOSFET), insulated gate bipolar transistors (IGBT) and similar high voltage switches which may be used in implantable pacemaker/defibrillators to deliver defibrillation shocks to a patient or recipient of the implantable medical device.

BACKGROUND OF THE INVENTION

In existing implantable arrhythmia control systems the high voltage switches are controlled by transformer coupled control signals. An example of an implantable arrhythmia control system is described in U.S. Pat. No. 4,960,123 to P. J. Maker, entitled "Differentiating between Arrhythmia and Noise in an Arrhythmia Control System". The transformer coupling techniques for controlling the high voltage switches in existing devices have been found to possess a number of disadvantages. These include the high volume of the coupling transformers, the cumbersome mechanical structure of these transformers and, additionally, the high susceptibility of the core of the transformer to external magnetic fields.

It is aesthetically advantageous, and of greater comfort to a patient or recipient of an implantable medical device, to reduce the volume and the weight of the device. Additionally, reducing the mechanical complexity of the components used in implantable devices not only reduces the cost but also improves the functional reliability of the system. It is of further advantage to the recipient of an implantable device to reduce the susceptibility of the device to magnetic interference which frequently occurs in normal living and work environments, as well as in hospitals or clinics, especially during the delivery of certain types of medical therapies and other treatments.

Accordingly, it is an object of the present invention to provide an improved circuit for driving high voltage switches in implantable pacemaker/defibrillators and other medical devices by incorporating capacitively coupled control signals in place of the transformer coupling techniques used in prior art pacemaker/defibrillators and other medical devices.

It is a further object of the invention to provide an apparatus which offers to patients or recipients of pacemaker/defibrillators and other implantable medical devices the advantages of lower costs, reduced volume, greater functional reliability and lower susceptibility to the hazards of electromagnetic interference.

It is a still further object of the invention to enhance the efficiency of such a device by the design of control circuitry which allows the output switch to be turned on and turned off in a very short time, thus preventing turn-on/turn-off transient currents from overheating the output switch with possible resultant damage to the switch. This is especially important in implantable medical devices to avoid damage to critical electronic components.

Another object of the invention is to provide a device for capacitive control of a high voltage output switch wherein the circuit has a very high common mode rejection ratio. As a result, the common mode switching high voltage transients do not lead to false switching of the high voltage switch. The invention aims to improve patient safety by the implementation of such a factor in its circuitry.

It is yet another object of the invention to reduce the peak current consumption of implantable defibrillator/pacemakers and other devices by providing a high voltage output switch driving circuit having reduced power consumption, thus preventing the output switch driving circuit from overloading the power supply. Hence, lower current, simpler design supplies can be used. As a result, by means of appropriate circuit implementation, a further reduction in volume of the implantable device is attainable.

SUMMARY OF THE INVENTION

Briefly stated, and in accordance with one embodiment of this invention, there is provided an implantable device for treating a malfunctioning heart. The device includes a high voltage circuit having a tank capacitor for storing therein during a charging mode of operation thereof high voltage DC electrical energy and for delivering such energy to a malfunctioning heart in the form of an electrical shock during a discharging mode of operation thereof, and means for supplying high voltage electrical energy to the tank capacitor. The device further includes a high voltage switch coupled to the high voltage circuit for switching, in the order of microseconds, the high voltage circuit between its charging and discharging modes of operation; a power supply for providing low voltage electrical energy for use in controlling the high voltage switch; a control circuit coupled between the power supply and the high voltage switch and capable of driving the high voltage switch to switch its output in the order of microseconds, for controlling the operation of the high voltage switch; and capacitors for capacitively coupling the power supply to the control circuit and electrically isolating the high voltage DC electrical energy from the power supply.

The control circuit includes a common mode switch for rejecting common mode noise, and an additional switch for rapidly changing the output state of the high voltage switch.

BRIEF DESCRIPTION OF THE DRAWINGS

Further objects, features, and advantages of the invention will become apparent upon consideration of the following detailed description in conjunction with the accompanying drawings, in which.

DETAILED DESCRIPTION

Figure 1:
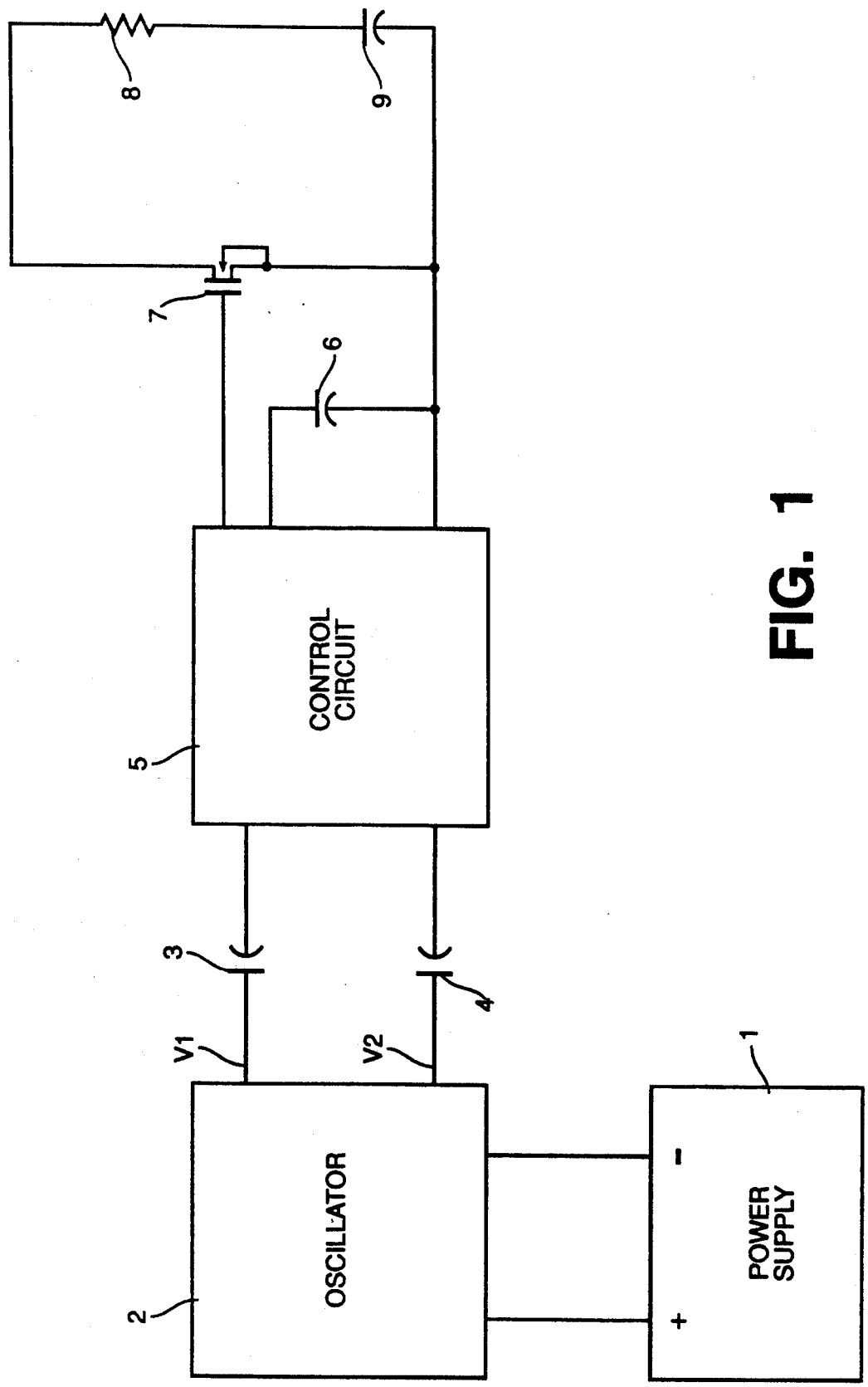
FIG. 1 is a block diagram of a circuit for driving a high voltage switch in accordance with the invention.

FIG. 1 depicts a block diagram of a circuit for driving a high voltage switch in accordance with the invention. In this figure, a square pulse oscillator 2 with two complementary outputs V1 and V2 is used to drive a control circuit 5 via respective coupling capacitors 3 and 4. These capacitors also provide high voltage isolation between the high voltage side of the circuit, including control circuit 2 and an output switch or switching transistor 7, and the low voltage side thereof, including a power supply 1 and oscillator 2.

The oscillator 2 gets its power from low voltage power supply 1. A capacitor 6 is charged to a voltage sufficient to drive the gate of output switch 7. This capacitor can be charged either directly from control circuit 5, or indirectly from an external source such as a high voltage tank capacitor 9, or a dedicated charging circuit (not shown).

Control circuit 5 appropriately connects capacitor 6 to the gate of output switch 7 to turn it on and deliver output defibrillation current from tank capacitor 9 to a load impedance 8. In accordance with one embodiment of the invention, when oscillator 2 is turned off, the voltage across capacitor 6 decays below the voltage threshold of the output switch 7, which turns it off. In accordance with an alternate embodiment of the invention, the control circuit senses the turning off of the oscillator and then disconnects capacitor 6 from the gate of output switch 7 to abruptly turn it off. Both of these circuit implementations are described in further detail below.

One of the main applications of the invention is in the field of implantable medical devices, such as implantable arrhythmia control systems which possess the capability of providing defibrillation therapy to a patient. Since the invention allows the integration of the control circuit and the high voltage switch into one system, the integrated high voltage system can be directly driven using low voltage signals without the need for coupling or isolation transformers. This integration has therefore resulted in facilitating the use of circuit components which take up considerably less space, providing a significant saving in the volume of implantable pacemaker defibrillators and other high voltage medical devices in which volume is a critical factor.

The aforementioned two alternative embodiments of the invention are designed to drive different types of switches. The first embodiment relates to a direct drive for high voltage switches with low input capacitance and voltage thresholds, such as found in the case of IGBT switches. The second embodiment relates to a second type of circuit for driving high voltage switches which require a higher input charge in order to turn them on. This second type of circuit is suitable for driving high power MOSFET switches used in medical applications and in other high voltage, high power, low duty cycle switching applications.

Figure 2A:
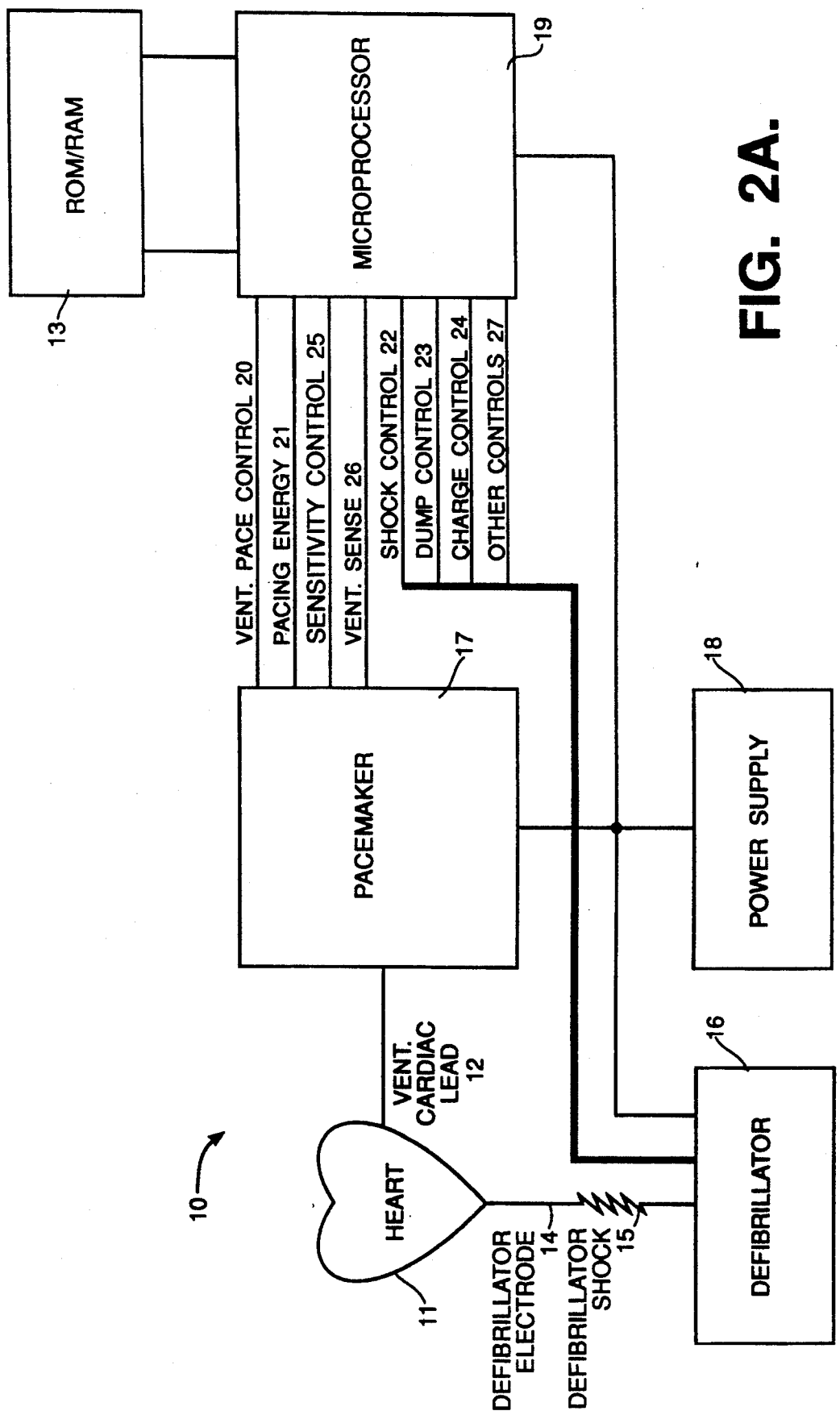
FIG. 2A is a block diagram of an implantable single chamber arrhythmia control system.

Referring to FIG. 2A, there is depicted a block diagram of a single chamber implanted arrhythmia control system or device 10. System 10 includes a ventricular cardiac lead 12 connected to the patient's heart 11; a pacemaker 17 for the detection of analog signals representing cardiac electrical activity and for the delivery of bradycardia or anti-tachycardia pacing pulses to the ventricular chamber of the heart; a microprocessor 19 which, in response to various inputs received from the pacemaker 17 as well as from a defibrillator 16, performs various operations so as to generate different control and data outputs to both the pacemaker 17 and the defibrillator 16; and a power supply 18 for the provision of a reliable voltage level. Defibrillator 16 produces a high voltage to charge its capacitors and then discharges them in response to control signals from the microprocessor 19. A defibrillator electrode lead 14 transfers the energy of a defibrillator shock 15 from the implanted arrhythmia control device 10 to the surface of the heart 11. A ROM/RAM unit 13 is also included in the device 10.

By way of definition for the arrhythmia control device as a whole, the term "cardioversion", as used herein refers to the discharge of electrical energy into cardiac tissue in an attempt to terminate or revert a tachycardia. It may range from a high (40 Joules or more) to a low (less than 1 Joule) of energy discharge. The discharge may be monophasic or biphasic but is not restricted to these waveforms. Cardioversion shocks may or may not be synchronized to the rhythm of the heart. "Defibrillation" is a particular example of cardioversion.

Microprocessor 19 receives various status and/or control inputs from pacemaker 17 and defibrillator 16, such as a ventricular sense signal on a ventricular sense line 26, performs operations such as arrhythmia detection, and produces outputs such as a ventricular pace control signal on a ventricular pace control line 20, which determine the type of pacing to take place.

Other control outputs generated by the microprocessor 19 include a ventricular pacing energy signal on line 21 which controls the pulse energy, a shock control signal on line 22 which signals that a shock is to be delivered to the patient, a dump control signal on line 23 which indicates that a shock is to be dumped at an internal load within the defibrillator, a charge control signal on line 24 which determines the voltage level of the shock to be delivered, a ventricular sensitivity control signal on line 25 which determines the sensitivity setting of the sensing circuits, and various other control signals shown generally on line 27.

Figure 2B:
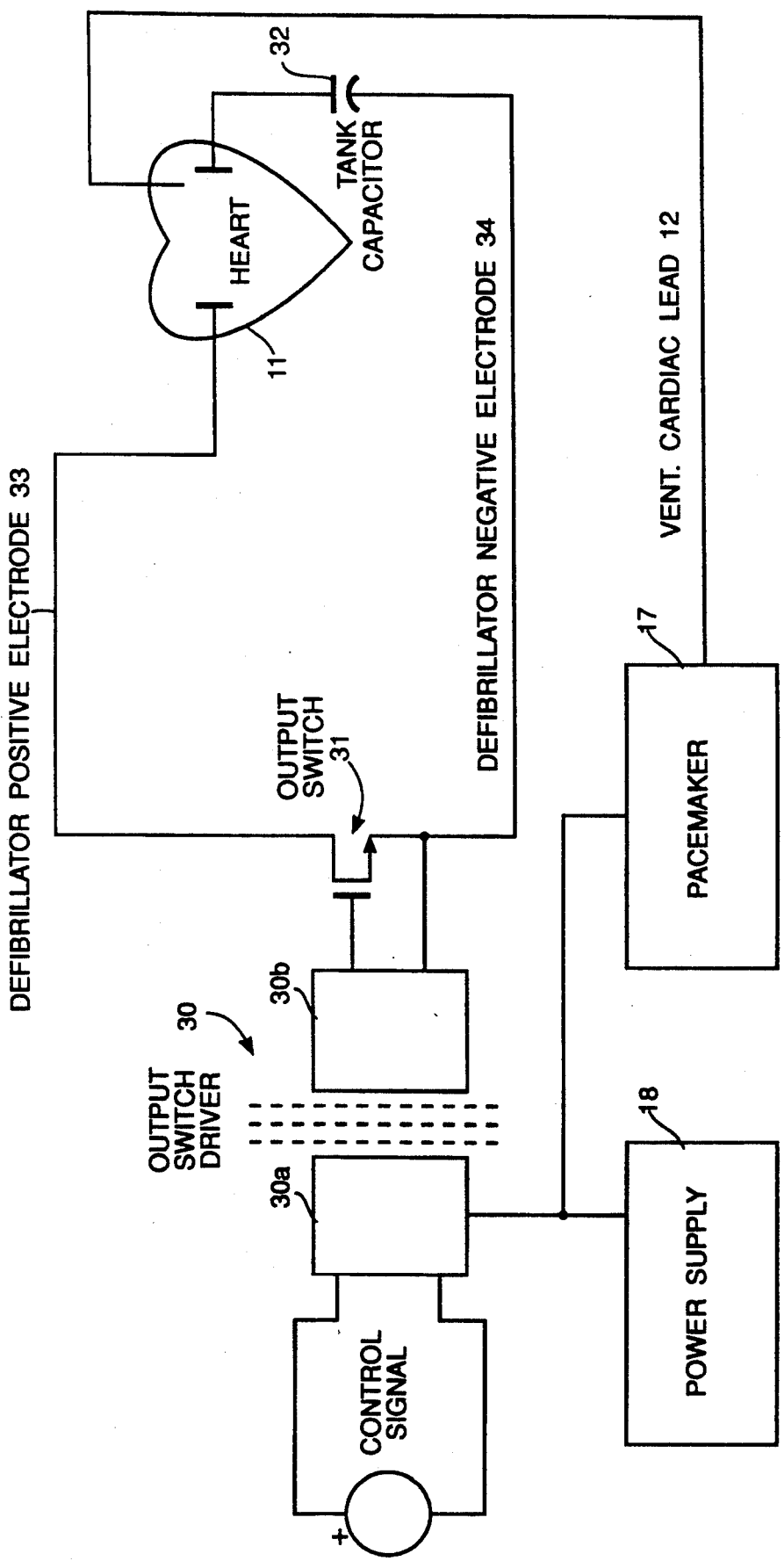
FIG. 2B depicts a circuit for driving the high voltage output switch of a defibrillator in a prior art implantable arrhythmia control system.

FIG. 2B depicts a circuit for driving a high voltage output switch 31 of a defibrillator in a prior art implantable arrhythmia control system. In this figure the power supply 18 drives both the pacemaker 17 and the low voltage section 30a of an output switch driver 30. Output switch driver 30 comprises two electrically isolated sections 30a and 30b. The first section 30a operates at low voltage and is referenced to the same common ground as power supply 18 and pacemaker 17. The second section 30b is electrically isolated from the low voltage section 30a; however, both sections are coupled in such a manner that the energy applied to the low voltage side is transmitted to drive the high voltage switch 31 on the high voltage side. Heretofore, the means of coupling used between the two sections has been the magnetic coupling of a transformer. In the present invention, capacitive coupling is employed between two sections which correspond to sections 30a and 30b. When the output switch 31 is turned on, it delivers the shock energy from a charged tank capacitor 32 to the heart 11.

The pacemaker pacing leads, including ventricular cardiac lead 12, are also connected to the heart, causing an electrical path to extend from the low voltage to the high voltage side of driver 30. As a result, during the delivery of defibrillation shocks, a high voltage will develop between the low and the high voltage sides of the driver. The isolation barrier between the two sections 30a and 30b of output switch driver 30 must be able to withstand this voltage.

Figure 3:
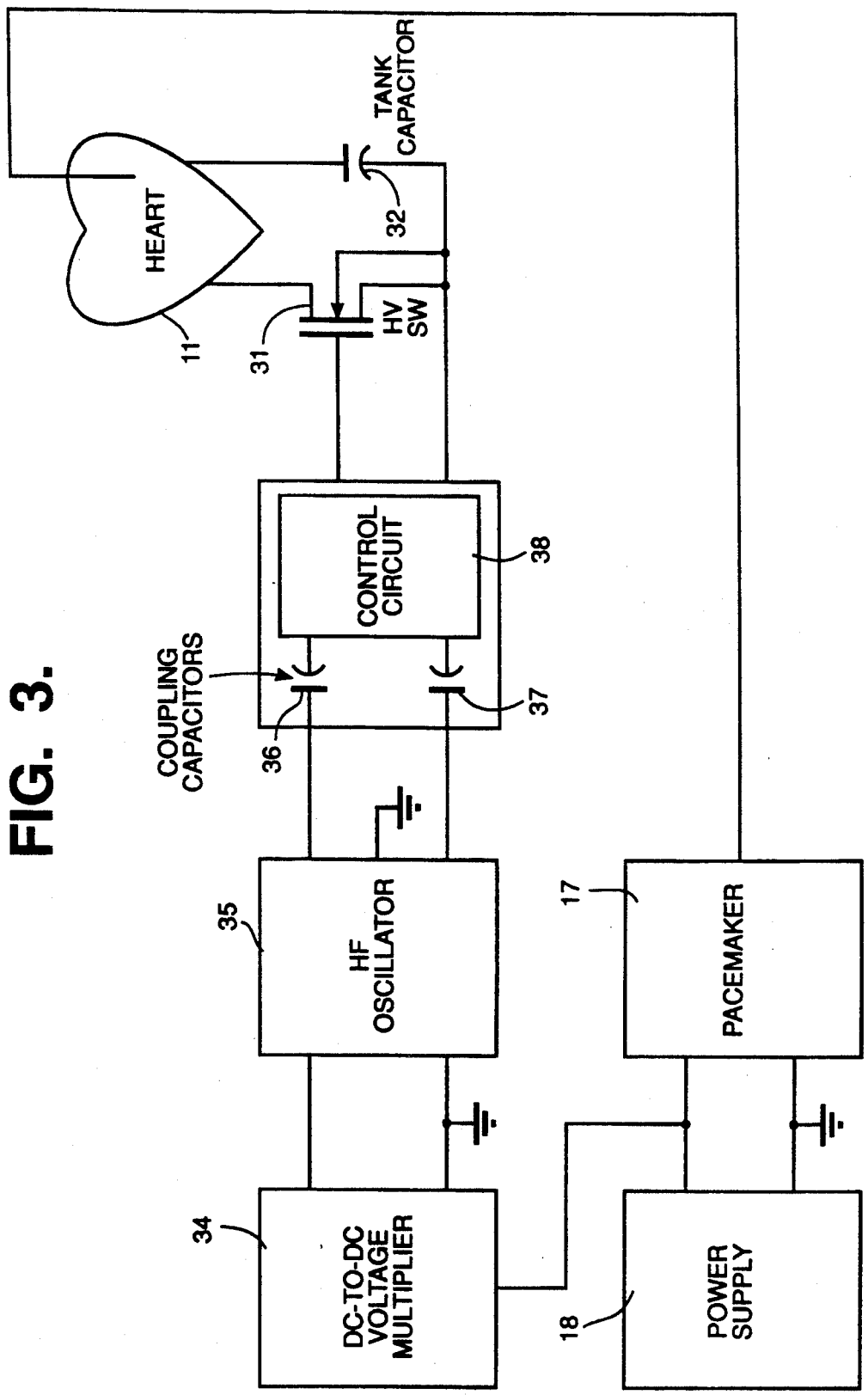
FIG. 3 is a block diagram, in greater detail than FIG. 1, of a capacitively driven high voltage switch circuit.

FIG. 3 depicts a capacitively driven high voltage switch circuit according to the invention. In this circuit the low voltage (e.g., 2.8 V) power supply 18 drives a DC-to-DC voltage multiplier 34. In the case of implantable pacemaker/defibrillators, power supply 18 also supplies DC current to the low voltage circuits, including the pacing and sensing circuits.

The DC-to-DC voltage multiplier 34 generates an output voltage that is 4 times the power supply voltage (i.e., 11.2 V with respect to the low voltage common ground). This voltage is used to drive a 20 MHz high frequency oscillator 35 to generate a 20 MHz square signal. Oscillator 35 is turned on only when it is required to turn on the high voltage output switch 31. Turning the oscillator off also turns off the high voltage output switch 31, as explained below.

The output of the high frequency oscillator 35 is coupled to a control circuit 38 via coupling capacitors 36 and 37. Capacitors 36 and 37 also isolate the low and high voltages sides of the FIG. 3 circuitry and carry the voltage difference between these sides. This is the difference in voltage between the ground on the low voltage side, and the reference terminal of the high voltage side. When the switch 31 is turned off, this voltage difference is equal to the voltage across the tank capacitor 32, which can be as high as 1000 V.

When the oscillator 35 is turned on, the current through the coupling capacitors 36 and 37 is rectified to generate the DC energy required to drive the control circuit itself as well as to turn on the output switch 31. When the oscillator is turned off, the DC voltage that powers the control circuit diminishes and the output switch 31 is turned off.

As will appear in greater detail below, the control circuit 38 is more complicated than just a rectifier circuit. It is essential that the control circuit be able to turn the output switch 31 on and off in a very short time so that the turn-on, turn-off transient currents do not overheat and damage the output switch. Another requirement is that the control circuit 38 must have a very high common mode rejection ratio such that the common mode switching high voltage transients do not lead to false switching of the output switch 31. A third requirement is that the power consumption of the control circuit must be low so that the circuit does not overload the power supply 18.

The present invention introduces a novel approach to designing a control circuit which satisfies the foregoing requirements. Two different control circuit implementations are described below with reference to two corresponding embodiments. Each of these embodiments suits a different type of high voltage switch.

Figure 4:
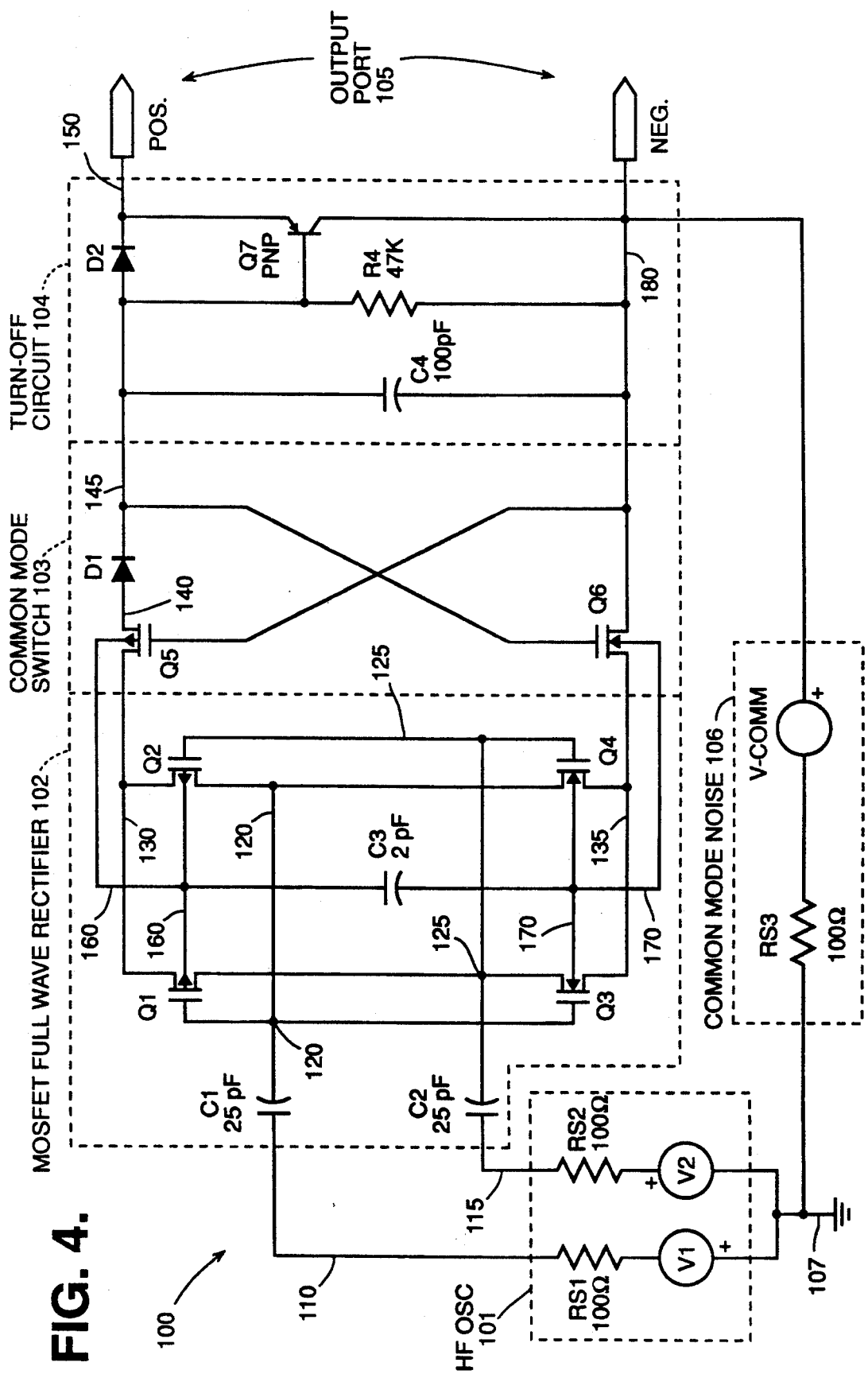
FIG. 4 is a schematic diagram of a direct drive control circuit according to one embodiment of the invention.

FIG. 4 depicts the first of the two control circuit embodiments described, and is referred to as the "direct drive" control circuit 100.

Circuit 100 is the simpler of the two embodiments and can be used to drive the input of a high voltage switch 31 (FIG. 3) that has a low input capacitance and a voltage threshold of about 5 V or less. This circuit is designed to charge a 5 nF input capacitance to 5 V in less than 10 μs.

This fast turn-on time is essential to protect the output switch against the turn-on transients. A fast turn off is achieved using a fast discharge circuit to deplete the input capacitance from its charge when the high frequency oscillator is turned off.

A high common mode rejection is achieved by using a full wave rectifier and a common mode switch, as explained below.

The direct drive control circuit 100 of FIG. 4 comprises six sections. These include a high frequency oscillator 101 having complementary outputs V1 and V2, a MOSFET full wave rectifier 102, a common mode switch 103, a turn-off circuit 104, an output port 105 that drives the inputs of the high voltage output switch 31 (FIG. 3), and a common mode voltage or noise 106 which occurs as a result of charging the high voltage tank capacitor 32 (FIG. 3), turning the high voltage output switch 31 (FIG. 3) on or off, or switching other high voltage signals in the defibrillator circuit.

Figure 5:
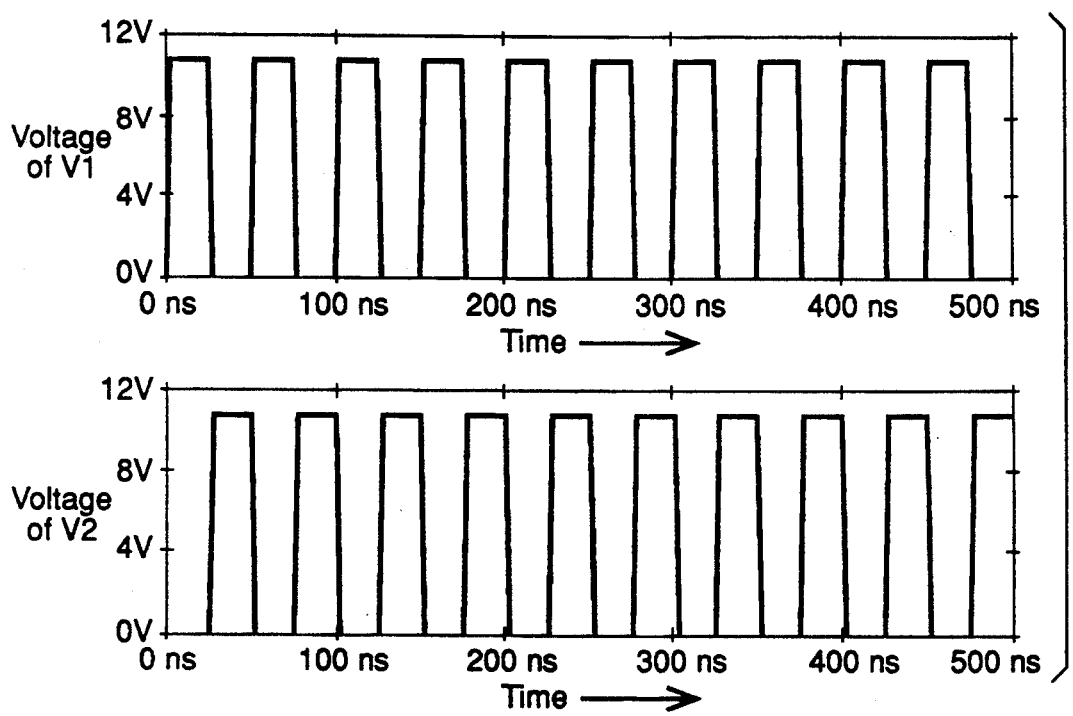
FIG. 5 shows the waveforms for complementary outputs of a high frequency oscillator employed in the invention.

In control circuit 100, node 107 is the ground or reference node for the low voltage side. As indicated above, the voltage sources V1 and V2 are the two complementary outputs of the high frequency oscillator 101. The voltage waveforms for voltages V1 and V2 are shown in FIG. 5. These are square pulses at 20 MHz with rise and fall times of less than 5 ns. Resistors RS1 and RS2 in oscillator 101 are the source of the impedance of the oscillator.

Capacitors C1 and C2 are high voltage coupling capacitors that couple the oscillator 101 outputs V1 and V2, respectively, to the inputs of the full wave rectifier 102. Capacitor C3 serves to sample and store a DC voltage bias for the P and N bulk material of the MOSFET transistors Q1, Q2, Q3 and Q4 of the rectifier circuit 102.

When the oscillator is enabled, current starts flowing to the output port 105, as follows. When the voltage V1 is high, i.e. at 11.2 V, V2 will be low, i.e. at zero volts with respect to the low voltage side ground node 107. These signals are coupled to the input nodes 120 and 125 via the capacitors C1 and C2. Node 120 is connected to the gates of MOSFETs Q1 and Q3 and to the sources of MOSFETs Q2 and Q4. The gates of MOSFETs Q2 and Q4 and the sources of MOSFETs Q1 and Q3 are connected to node 125. When node 120 is more positive than node 125 by more than the voltage thresholds of MOSFETs Q2 and Q3, these two transistors will be turned on, allowing current to flow out of the drain of MOSFET Q2's node 130 and back through the drain of MOSFET Q3's node 135. When node 125 is more positive than node 120, the current still flows out of node 130 and back into node 135, but through MOSFETs Q1 and Q4. Therefore, the output current at node 130 is the full wave rectified current of capacitors C1 and C2.

Once the voltage across a capacitor C4 in turnoff circuit 104 exceeds a diode forward voltage drop, the diode D1 conducts and the current flows through the positive terminal POS of output port 105 to the load (not shown), then back through the negative terminal NEG of the output port.

The high common mode rejection of control circuit 100 depends on a matching of the separate, similar components utilized therein, including the coupling capacitors. Therefore, for the best results, the integrated circuit components should be manufactured using a suitable twin-tub high voltage IC process (See, for example, the twin tub structure and process illustrated and described at page 111 of the book "Custom-Specific Integrated Circuits," by Stanley L. Hurst, published in 1985 by Marcel Dekker, Inc., 270 Madison Avenue, New York, N.Y. 10016).

Common mode switch 103 stops the flow of current caused by common mode voltages 106. It allows the current to flow to the output port 105 only if enough differential voltage is applied to the circuit inputs (nodes 120 and 125). The operation of switch 103 is explained below.

One of the important properties of control circuit 100 of FIG. 4 is that high common mode rejection can be achieved even if the source-to-bulk and drain-to-bulk junctions of the transistors break down at voltages much lower than the applied common mode voltage. In the circuit of FIG. 4 the breakdown voltage of the source and drain junctions of the N-channel MOSFET's is 20 V. The breakdown voltages for the P-channel source and drain junctions is 25 V. The P-to-N bulk breakdown voltage is 30 V. It is shown further in the description below that the circuit is able to withstand +/−1000 V common mode voltages without conducting any significant current to the load.

To explain the operation of the circuit of FIG. 4, particularly with respect to turning on high voltage output switch 31 (FIG. 3), let us assume that on the nth half cycle after turning oscillator 101 on, voltage V1 is high while voltage V2 is low (i.e., equal to zero). At the end of this half cycle, the sum of the voltages across capacitors C1 and C2, neglecting the drain-to-source saturation voltage of the "on" transistors, can be expressed as:

$$V_a(n) = V_1 - V_4(n) - V_d$$

where V4(n) is the voltage across C4 at the end of the nth half cycle, and Vd is the forward voltage drop of the diode D1.

At the onset of the (n+1)th half cycle, V1 drops to zero and V2 goes to its peak value. The voltage V2 is then added in phase to the voltage across capacitors C1 and C2. Thus the sum of the voltages between nodes 140 and 180 exceeds the voltage across capacitor C4 and current will flow through diode D1 to increase the charge on capacitor C4.

Solving for the voltage across capacitor C4 and assuming the initial condition that V4(0)=0, we obtain:

$$V_4(n) = 0.5(V_1 + V_2 - 2V_d)\left(1 - \left[\frac{(C_4(C_1+C_2) - C_1C_2)}{(C_4(C_1+C_2) + C_1C_2)}\right]^n\right)$$

This equation can be re-written in the exponential form:

$$V_4(n) = 0.5(V_1 + V_2 - 2V_d)\left(1 - \exp\left(\frac{-t}{(R_{eq}C_4)}\right)\right)$$

When capacitor C4 is much larger than the series combination of capacitors C1 and C2, the equivalent resistance Req is approximately given by:

$$R_{eq} = \left(\frac{T_{os}}{4}\right)\left[\left(\frac{1}{C_1}\right) + \left(\frac{1}{C_2}\right)\right]$$

where Tos is the period of oscillation of the high frequency signal. In the circuit of FIG. 4 this period is 50 ns. Thus the series combination of capacitors C1 and C2 can be replaced by an equivalent resistance of 1 K.

In addition to this equivalent resistance of the coupling capacitors C1 and C2, the output resistance of oscillator 101, the "on" resistance of each of the MOSFET transistors Q1 to Q6, which is about 100 R, and the diode D1 series resistance have to be considered. The total equivalent series resistance of the circuit of FIG. 4 adds up to about 1.5 K.

To continue this simplified circuit analysis, we shall assume that the loading capacitance of the gates, sources and drains of the four MOSFET transistors Q1 to Q4 is about 10% of the value of capacitor C1 (or C2). The effective input voltage is then 10% less than the applied 11.2 V. For simplicity we shall assume that the effective input voltage is 10 V peak.

When considering the charging of, for example, a 1 nF capacitor, in parallel with the 100 pF capacitor C4, from a 10 V DC source via a 1.5 K resistance, the voltage across the capacitor is then given by:

$$V_c = 10\left(1 - \exp\left(\frac{-t}{CR_{eq}}\right)\right)$$

This voltage reaches 5 V at t=0.69 RC=1.06 μs. This result of the mathematical model is in close agreement with the result, shown in FIG. 6, obtained by simulating the actual circuit of FIG. 4 in the charging of a 1 nF capacitor.

When this circuit is used to drive a high voltage switch having a voltage threshold of less than or equal to 5 V, and an effective input capacitance during switching of 5 nF, the turn on time of the high voltage switch will be about 5 μs.

To achieve this fast switching time, the circuit consumes heavy initial input current. This current is equal to the current needed to charge the input capacitance of the high voltage switch, plus the switching current losses. The current taken from the power supply is four times higher due to the DC to DC conversion ratio.

Figure 6:
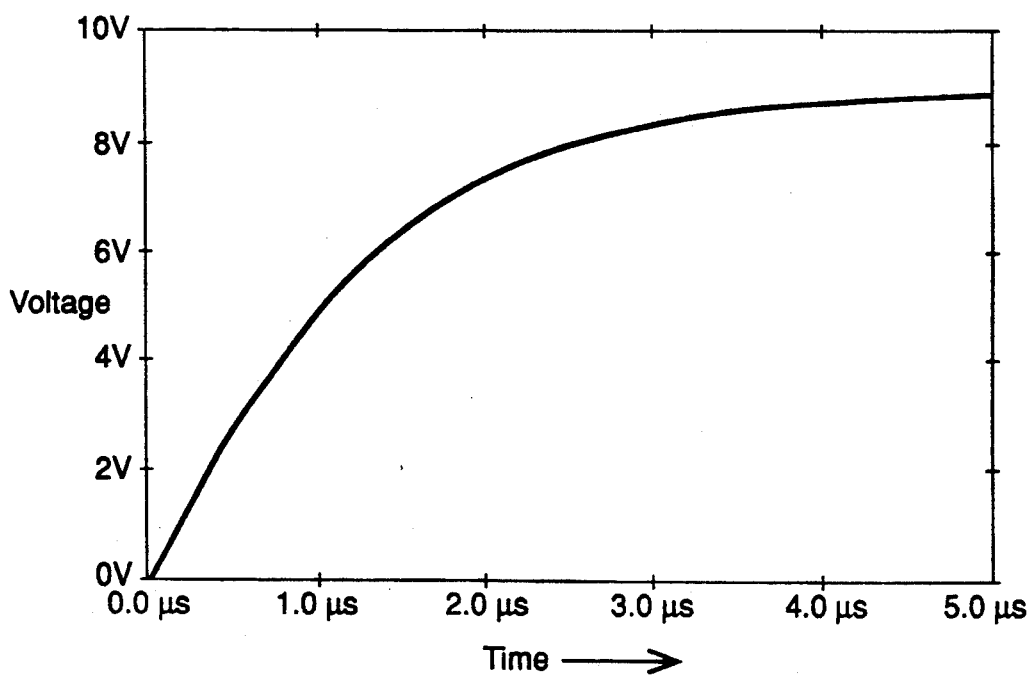
FIG. 6 shows the output voltage with respect to time when charging a 1 nF capacitor using the direct drive control circuit of FIG. 4.

As an example, to charge a 1 nF capacitor to 5 V in 1.1 μs, as shown in FIG. 6 above, the charging current will be:

$$Ich = C\frac{dv}{dt} = 4.55 \text{ mA}$$

Figure 7:
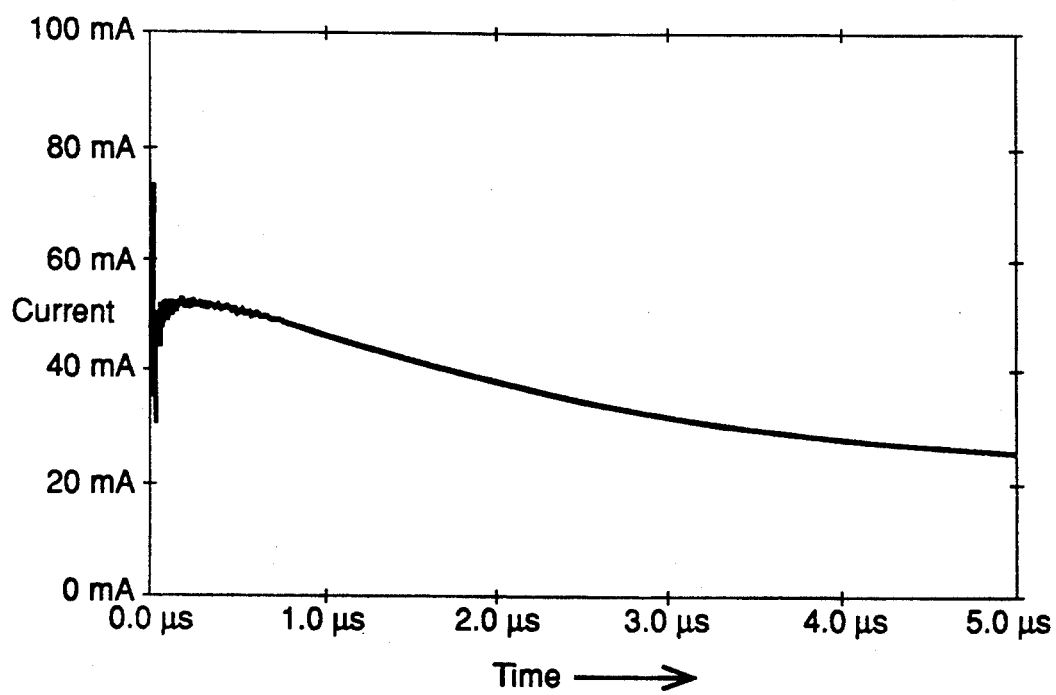
FIG. 7 shows power supply current with respect to time when charging the 1 nF capacitor.

In addition, a current of 0.45 mA is needed to charge the 100 pF capacitor C4 (FIG. 4). The switching of the different nodes of the circuit between +/−10 V at a rate of 20 MHz also consumes some current (about 5 mA). If the sum of the capacitance of all nodes is about 10 pF, the current losses will be an additional 4 mA. Thus the total input current at the start of the charging period will be about 14 mA. This is equivalent to 56 mA drawn from the 2.8 V power supply. This is in agreement with the power supply current consumption shown in FIG. 7, obtained using the actual circuit of FIG. 4 in connection with charging a 1 nF capacitor.

After charging the load capacitance the power supply current drops from 56 mA to about 16 mA, which represents the switching losses. This 16 mA current consumption is only required for a few milliseconds, the duration of the defibrillation shock in implantable defibrillators. Provided that the power supply can provide this current for this short period, this high current consumption can be tolerated.

The mechanism of switching on the high voltage switch 31 (FIG. 3) was explained above. The following discussion relates to operation of the turn-off mechanism. When the high frequency oscillator 101 (FIG. 4) runs for a few tens of micro-seconds, the turn-off circuit capacitor C4, as well as the input capacitance of the high voltage switch 31, will be fully charged to about 9 V.

Figure 8:
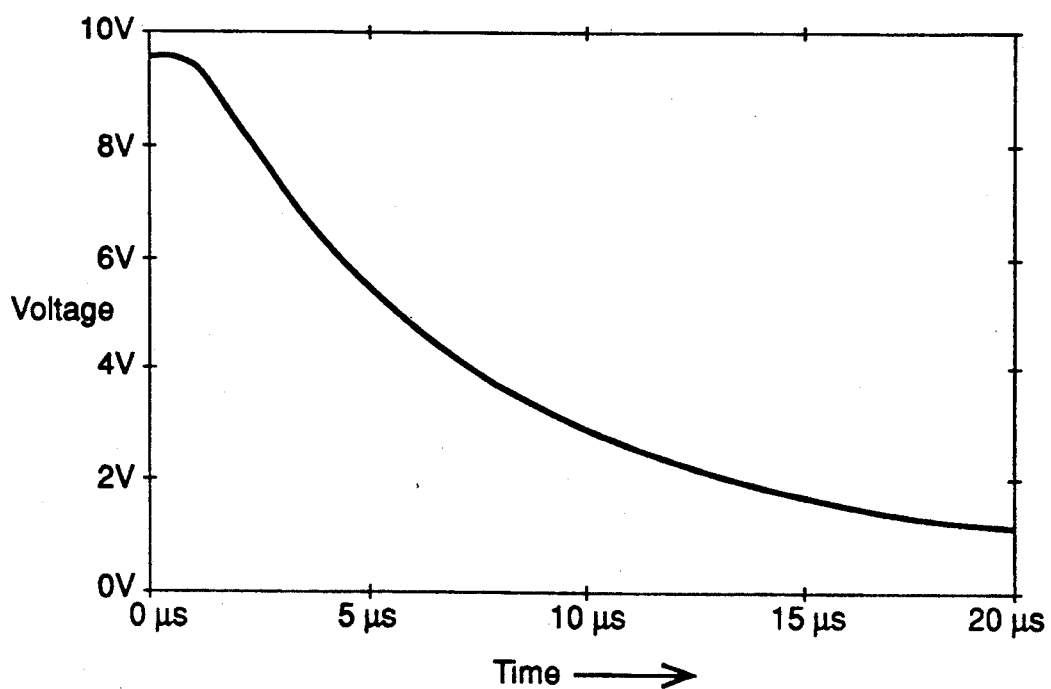
FIG. 8 shows the discharge waveform of the 1 nF capacitor.

When the oscillator 101 is turned off, the voltage across turn-off circuit capacitor C4 decays due to the current that flows through a resistor R4 in turnoff circuit 104. When the voltage across capacitor C4 drops by 0.6 V below the voltage of an output node 150, a bipolar transistor Q7 in the turn-off circuit conducts, discharging the load capacitance at the same rate that capacitor C4 discharges via resistor R4 (i.e., with a discharge time constant of 4.7 μs, which is independent of the load capacitance). The discharge waveform of a 1 nF load capacitance is shown in FIG. 8.

Figure 9:
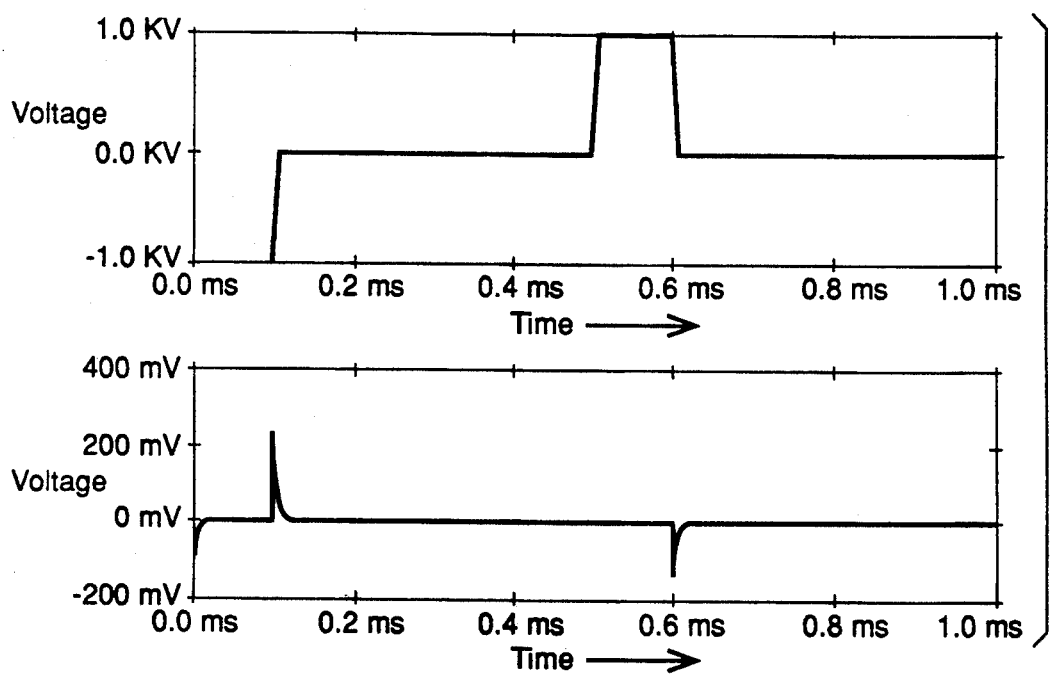
FIG. 9 shows the voltage waveform of +/−1000 V, 100 μs, common mode pulses applied to a turn-off circuit capacitor, and the response of the capacitor to such pulses.

A discussion of the common mode rejection properties of the control circuit 100 of FIG. 4 will now be presented. To demonstrate the high common mode rejection properties of the circuit, a 1000 V, 100 μs, square pulse, common mode voltage V-COMM is applied via a common mode noise circuit 106, as shown in FIG. 4. The output port 105 is left unloaded (the worst case condition) and the voltage across C4 is computed. The common mode voltage waveform, and the response of capacitor C4 thereto, are shown in the upper and lower graphs, respectively, of FIG. 9.

Figure 10:
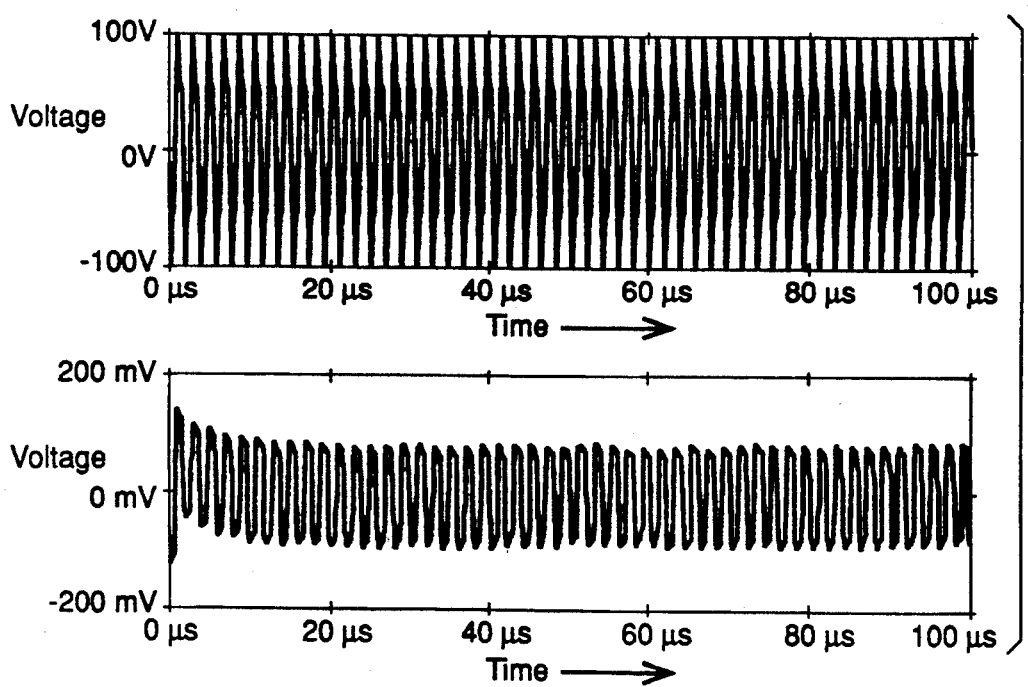
FIG. 10 depicts the response of the 1 nF capacitor to continuous common mode noise.

Similarly, FIG. 10 shows, in the lower graph, the response of turn-off capacitor C4 to continuous mode noise, shown in the upper graph. The continuous mode noise is represented by the application of a 200 V peak-to-peak, 500 Khz sine wave, common mode signal in series with a 50 pF source capacitance, which replaces resistor RS3 in the circuitry shown in FIG. 4. In both cases (FIGS. 9 and 10), the capacitor C4 is charged to a small voltage of less than 300 mV peak, which can not cause false turning on of the MOSFET high voltage output power switch 31 (FIG. 3).

This high common mode rejection can be practically achieved if the following requirements regarding the circuitry of FIG. 4 are satisfied:
1. The transistors Q1 and Q2 should have substantially identical electrical and breakdown characteristics. The breakdown voltages of the drain and source junctions of P-channel transistors are assumed, in this model, to be 25 V.
2. The transistors Q3 and Q4 should have substantially identical electrical and breakdown characteristics. The breakdown voltages of the drain and source junctions of N-channel transistors are assumed, in this model, to be 20 V.
3. It is preferable to use transistors with higher breakdown voltages if the IC process allows this. In the circuit of FIG. 4, the P-channel transistors must have higher breakdown voltages than the N-channel transistors.

Assuming that a common mode signal 106 is applied in the manner shown in FIG. 4, the operation of control circuit 100 will now be considered. As was explained above, the control circuit 100 conducts current in the correct direction to charge capacitor C4, and the gate capacitance of the MOSFET high voltage output switch 31 (FIG. 3), only if there exists a high enough differential voltage between nodes 120 and 125 to turn the bridge transistors Q1 to Q4 on or off, as appropriate to perform full wave rectification.

On the application of common mode voltage 106, common mode switch 103 does not allow any current to flow through capacitors C1 and C2 as long as the applied voltage is less than the breakdown voltages of the junctions of transistors Q1-Q7. If current is allowed to flow through these capacitors, then differential voltages may build up due to mismatches between the capacitors or between the current components connected through them. If this occurs, then the bridge transistors may be falsely turned on, and positive charging of C4 may occur. For this reason, the common mode switch 103 is used to stop the flow of current due to common mode voltages. However, when the voltage reaches the transistor breakdown voltages, conduction will occur, but the voltages across the capacitors C1 and C2 will be clamped to the same value and no voltage difference between node 120 and 125 will be generated For this equal voltage clamping to occur, transistor Q1 must match transistor Q2 and transistor Q3 must match transistor Q4.

Let us first consider the case where the capacitor C4 in FIG. 4 is fully discharged, and that a positive common mode voltage 106 is applied. In this case all of the terminals of the transistors Q1 to Q4 will be at zero volts. Node 180 will have a positive voltage that rises with the applied common mode signal. Nodes 145 and 150 will initially have the same voltage as node 180. In this case node 180 becomes the drain of transistor Q6, which is at the same voltage as the gate that is connected to node 145. Thus, transistor Q6 tries to conduct current from node 180 back to node 135. But this current can not flow anywhere because the gates and sources of the transistors Q3 and Q4 are both at zero volts. Thus, these transistors are turned off. Note here that because node 180 is the most positive node in the circuit due to the applied common mode voltage, node 135 will also be positive with respect to nodes 120 and 125. Therefore, node 135 becomes the drain node for transistors Q3 and Q4. (The drains and sources of different transistors are interchangeable and can be defined only depending on the amplitudes and polarities of the applied voltages.) On the other hand transistor Q5 has node 140 as its source. Both the gate and source of transistor Q5 are at the same positive voltage as nodes 180 and 145. This transistor is then turned off and can not conduct any current to the sources of transistors Q1 and Q2 (node 130 in this case).

When the common mode voltage 106 is negative, the transistor Q5 is then turned on with node 140 becoming the drain. But the transistors Q1, Q2, and Q6 stop the current from flowing through the input capacitors C1 and C2.

The second case to consider is when the capacitor C4 is charged to a voltage high enough to turn on both transistors Q5 and Q6. In this case both of these devices are turned permanently on, and current conduction due to common mode voltages can occur. The current may flow from node 130 to node 145 or vice versa. The direction of the current depends on the amplitude and polarity of the applied common mode voltage, as well as the simultaneous existence of a differential voltage between nodes 120 and 125. The diode D1 is inserted to stop any reverse current, due to common mode voltages, from discharging the capacitor C4.

Figure 11:
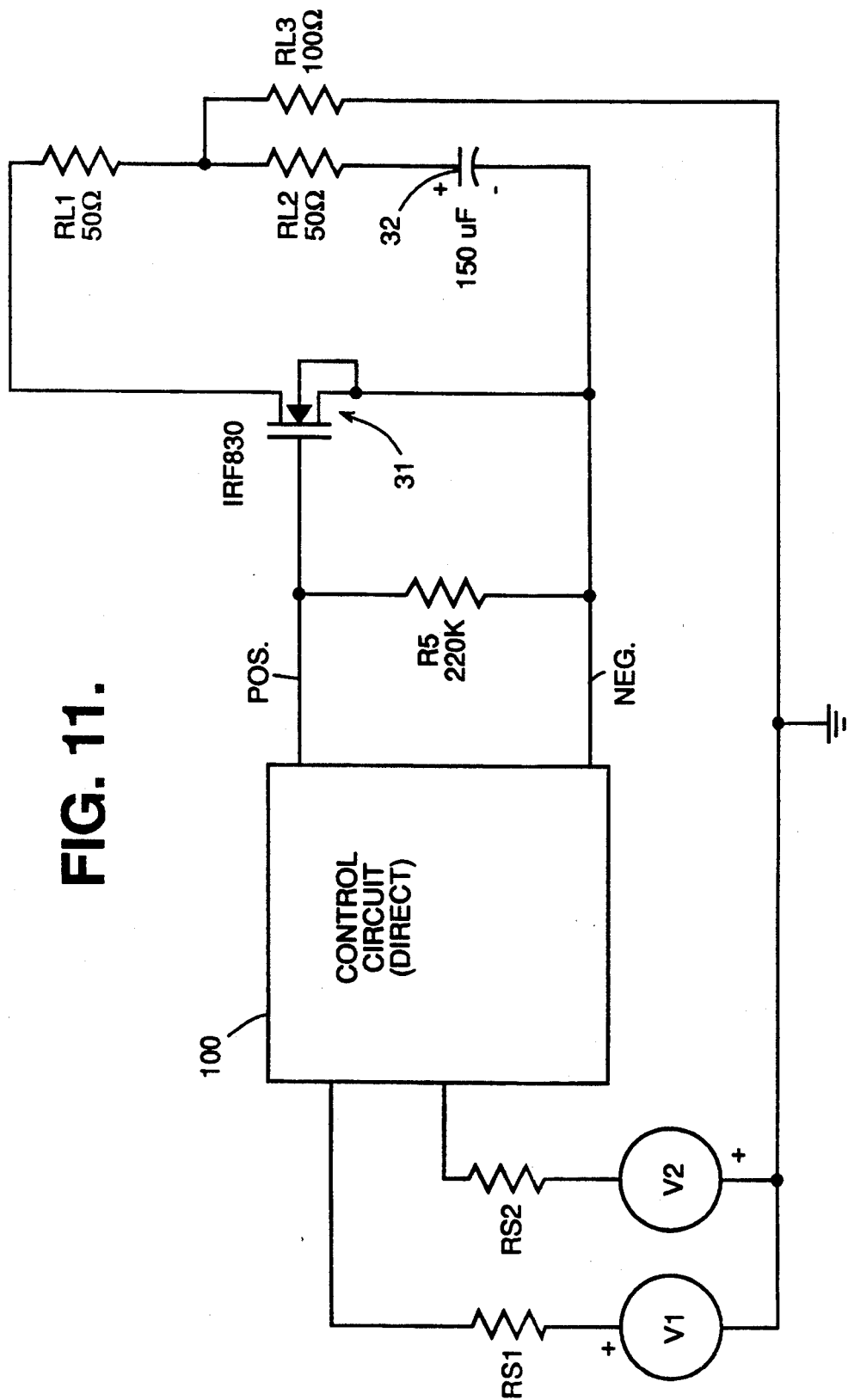
FIG. 11 depicts a circuit for driving a high voltage output MOSFET.

Referring to FIG. 11, the test circuit shown therein was simulated to determine the turn-on and turn-off times involved when the direct drive control circuit 100 is used to drive a high voltage output switch 31 that comprises a MOSFET device type IRF830. To simulate the operating conditions of an implantable defibrillator, a star-connected load is used, comprising resistors RL1, RL2 and RL3. In this load circuit the resistors RL1 and RL2 simulate the defibrillation impedance of the heart. The third resistor, RL3, represents the coupling from the heart to the low voltage side of the circuit through the pacing/sensing circuit of the implantable defibrillator.

In addition to testing the ability of the control circuit to turn the MOSFET output switch 31 on and off in a short time, the test is also used to confirm the high common mode rejection of the circuit, and to prove that common mode voltage disturbances during switching will not lead to false operation.

It is assumed that the tank capacitor 32 is initially charged to 500 V, the junction of resistors RL1, RL2 and RL3, the star-point of the resistive load, is at zerovolts with respect to the low voltage side ground, and that the NEG terminal is initially at −500 V with respect to ground. When the output transistor 31 is turned on, the voltage of the NEG terminal becomes −250 V with respect to ground, introducing a common mode voltage step of 250 V to the high voltage side. Also, when the switch 31 is turned off a negative common mode voltage step will occur. It is essential that these voltage disturbances do not affect the operation of the control circuit or lead to false switching of the high voltage output switch 31.

Figure 12:
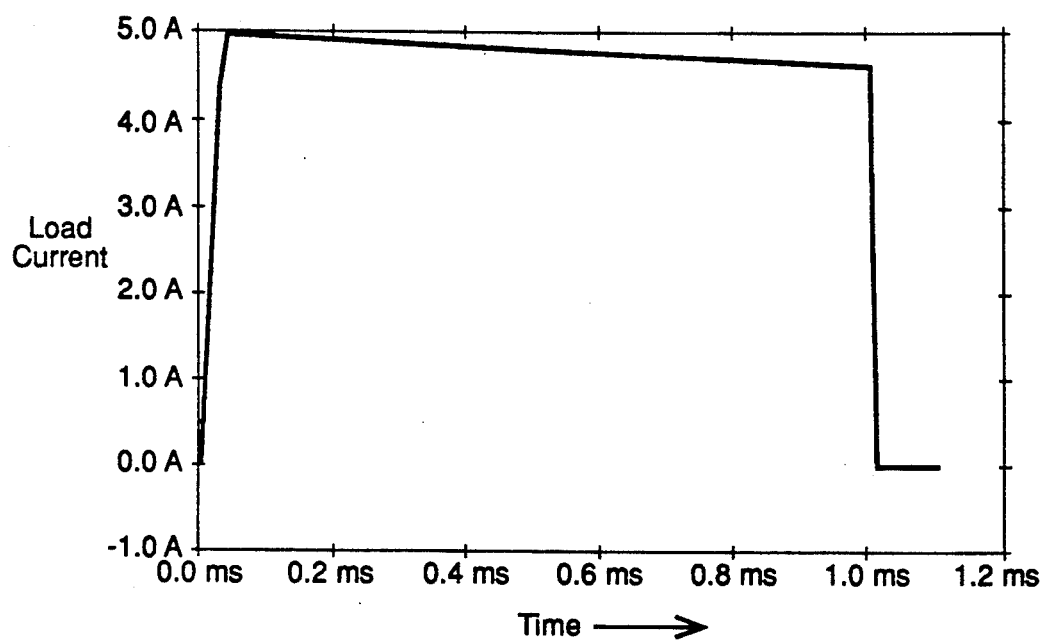
FIG. 12 graphically depicts the output load current waveform of the circuit of FIG. 11.

The voltages V1 and V2 are the outputs of the high frequency oscillator 101 (FIG. 4), as explained before. In this test the oscillator is turned on for 1 ms then turned off to turn the output transistor 31 on and to deliver a 5 A, 1 ms defibrillation current pulse through the defibrillation impedance RL1 and RL2. The current waveform through the output load RL1, RL2 and RL3, and its rise and fall times, are shown in FIG. 12.

Figure 13:
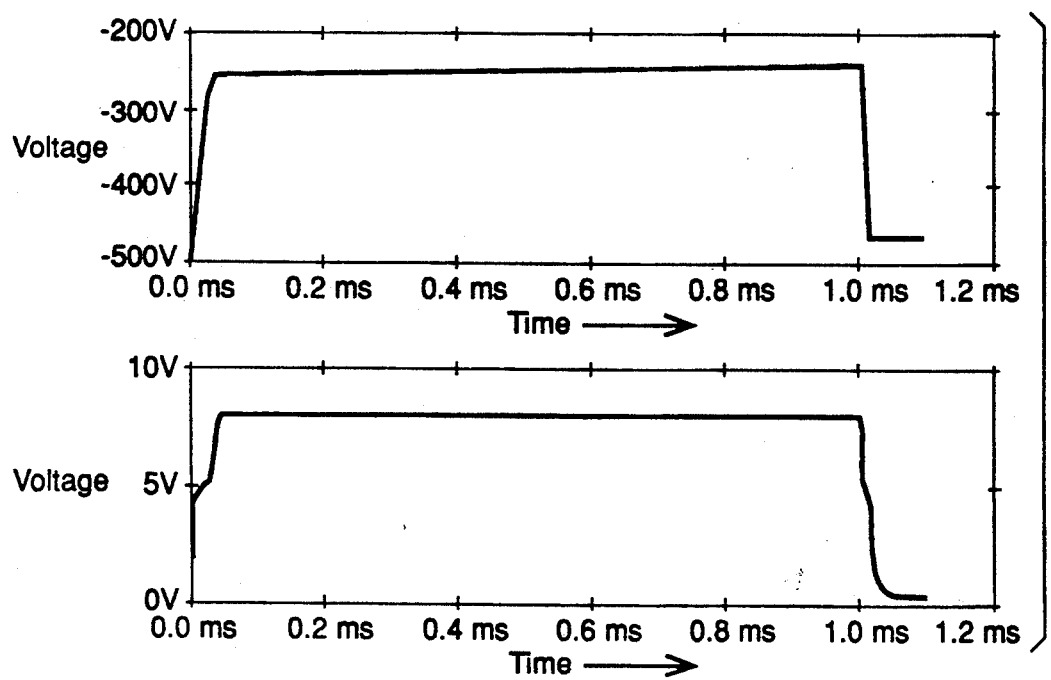
FIG. 13 graphically depicts the effect of the common mode voltage disturbances.

FIG. 13 shows, in the upper view, the common mode voltage disturbances which occur during switching of the output switch 31 and, in the lower view, their effect on the gate-to-source voltage of the output switch transistor 31. As shown in the lower view, the slope of the rising edge of the gate voltage is not constant due to the loading effect of the input capacitance when the transistor is turned on (Miller effect). The common mode voltage transients themselves did not affect the gate voltage.

Figure 14:
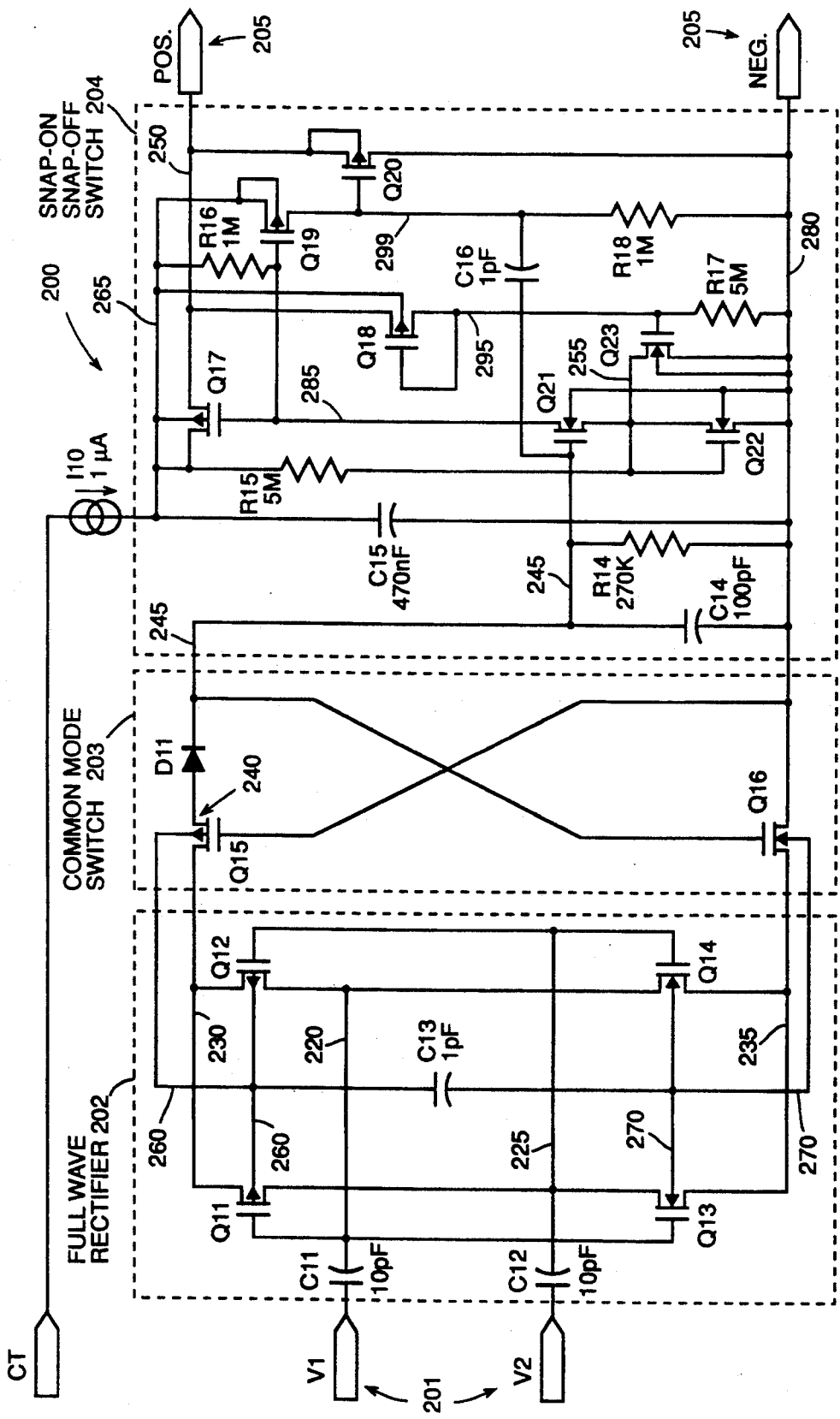
FIG. 14 is a circuit diagram of the control circuit of another embodiment of the invention which utilizes an indirect drive control circuit.

Referring now to FIG. 14, an indirect drive control circuit has there been illustrated generally at 200. Indirect drive control circuit 200 is different from direct drive control circuit 100 (FIG. 4) in the way that the turn-on charge of the high voltage output switch 31 (FIG. 3) is provided. In the direct drive circuit 100 this charge is obtained from the rectified oscillator current. In the indirect drive control circuit 200 this turn-on charge is supplied by an initially charged capacitor C15. This capacitor can be charged to the required voltage (about 15 V) from the high voltage tank capacitor via terminal CT or from a separate charging circuit (not shown). This separate charging circuit can be similar to the direct drive control circuit 100 of FIG. 4 but driven from a higher oscillator voltage. Other charging circuits can also be used. The values of capacitor C15 and its charging voltage depend on the input capacitance of the high voltage switch 31 (FIG. 3) that is to be controlled. In this example it is assumed that the high voltage switch 31 has a voltage threshold of about 10 V and that its Miller capacitance during switching can be as high as 50 nF.

The indirect drive control circuit 200 of FIG. 14 comprises three building blocks, including a full wave rectifier 202, a common mode switch 203, and a snap-on, snap-off switch 204. The functions and operations of the full wave rectifier 202 and the common mode switch 203 are similar to those that have been explained earlier in connection with the direct drive control circuit 100 of FIG. 4. The new circuit component, the snap-on, snap-off switch 204, is controlled by the voltage across capacitor C14, which is charged from a square wave signal oscillator (not shown) via the full wave rectifier 202 and the common mode switch 203. (The square wave signal oscillator in effect replaces the high frequency oscillator 101 of FIG. 4). When the voltage across capacitor C14 reaches the "on" threshold, a transistor Q21 will be turned on which will, in turn, turn on a transistor Q17. The latter transistor connects the charged capacitor C15 to the POS output terminal of an output port 205, which is in turn connected to the gate of the MOSFET high voltage output switch 31 (FIG. 3). When the square wave signal oscillator is turned off, the voltage across capacitor C14 decays to an "off" threshold, at which transistor Q17 is turned off and a transistor Q20 is turned on, shorting the POS and the NEG terminals of output port 205 to rapidly turn off the high voltage switch.

The advantages of the indirect drive control circuit 200 embodiment include the ability to drive large output switches; very fast turn-on and turn-off times; the ability to be driven from a low frequency (2 MHz), low amplitude (5.6 V) oscillator circuit, thus reducing the DC power requirements; and that it utilizes the same common mode rejection arrangement as used in the direct drive control circuit 100 (FIG. 4) embodiment.

Returning to a detailed consideration of the operation of the snap-on, snap-off switch 204, square wave oscillator signals V1 and V2 are only used to charge the 100 pF capacitor C14. The voltage V14 across this capacitor at a time t after turning the oscillator on (where t=n/2f, n is a negative integer and f is the frequency of the oscillator), is given by by the equation:

$$V14(n) = \left[\frac{(V1 + V2 - 2Vd)KC}{C(1 + K + C14(1 - K))}\right] \cdot \left[1 - \left(\frac{K(C14 - C)}{C14 + C}\right)2ft\right]$$

$$\text{where } K = \exp\frac{-1}{((2f \cdot R14(C + C14)))}$$

$$C = \frac{(C11)(C12)}{(C11 + C12)}$$

and n = number of half that have occurred since turning the oscillator on.

Substituting the values given in FIG. 14 for the capacitors, and assuming that the frequency of oscillation is 2 MHz, we obtain:

$$V14(t) = 0.915[0.5(V1 + V2) - Vd]\left[1 - \exp\frac{-t}{(2.2956 \mu s)}\right]$$

Therefore, for the voltage across capacitor C14 to reach a turn-on threshold of VON, a turn-on delay of TON will be encountered. This turn-on delay is then given by:

$$TON = -2.2965\ln\left[\frac{1 - 2VON}{(0.915(V1 + V2 - 2VD)))}\right]\mu s$$

Assuming that V1=V2=5 V, Vd=0.6 V, and VON =3 V, the turn-on delay will be about 3.14 μs. This is the delay after which the snap-on switch will be triggered.

The turn-off delay, on the other hand, is the time required for capacitor C14 to be discharged from its full voltage down to a turn-off threshold. From the above equations we conclude that this capacitor can be charged up to a final voltage of 0.915(V1+V2−2Vd)/2=4.026 V. When the oscillator signal is stopped, the charge on capacitor C14 will be dissipated through R14 with a time constant of 27 μs. Therefore, the time delay for the voltage on this capacitor to decay to a turn-off threshold of, say, 1.5 V will be about 27 μs. This is the time delay after which the snap-off switch function will be triggered. This time delay is not the fall time of the load current.

The fall time is much smaller and depends on the "on" resistance of transistor Q20. The turn-off delay can be made smaller by reducing the value of capacitor C14, but this will also reduce the common mode rejection of the circuit. The turn-off delay can also be reduced by using a smaller value for resistor R14. The effect of that change will be to increase the turn-on delay and reduce the final steady state voltage to which capacitor C14 can be charged from a given oscillator signal. This can be compensated for by operating at higher frequencies, or using higher amplitude signals. As for implantable defibrillator applications, turn-off delays of up to 100 μs are acceptable. The manner in which the decay of the charge on capacitor C14 triggers the snap-off switch function is described in greater detail below.

The snap-on, snap-off switch 204 has a series transistor Q17 to connect the charged capacitor C15 to the output node 250 of the POS terminal when the switch is turned on. When the switch is turned off, a shunt transistor Q20 clamps the voltage of the POS terminal to that of the NEG terminal of output port 205. Fast, bounce free, switching is achieved by positive hysteresis provided by a capacitor C16, and also by a transistor switch Q23.

When the square wave oscillator is turned on, capacitor C14 will be charged up as explained earlier. Once its voltage reaches the sum of the voltage thresholds of transistors Q21 and Q22, these transistors will be turned on, drawing current through a resistor R16. When the voltage across resistor R16 exceeds the voltage threshold of transistor Q17, this transistor will be turned on connecting capacitor C15 to the POS terminal of output port 205. In the meantime transistor Q19 will also be turned on, connecting the gate of a P-channel transistor Q20 to capacitor C15 and thus keeping transistor Q20 in the off state. When the voltage of the POS terminal exceeds the sum of the thresholds of transistors Q18 and Q23, the latter transistor will be turned on, shorting the drain and source of transistor Q22 and increasing the gate-to-source voltage of transistor Q21 to turn it hard on. This positive hysteresis ensures the fast turn on of the transistor Q17 and also masks any small changes in the voltage across capacitor C14 that may be caused by common mode noise resulting from turning on the high voltage switch 31 (FIG. 3). The capacitor C16 also introduces small positive hysteresis sufficient to guarantee fast bounce-free transition.

When the snap-on, snap-off switch 204 is turned on it consumes a small current through the resistors R15 to R18. This is equivalent to connecting a resistive load of 417 K across capacitor C15. This forms an RC circuit with a time constant of 196 ms. Therefore, if switch 204 is left on for 20 ms, the voltage across capacitor C15 will only drop to 90% of its value as a result of the current through the above-mentioned resistors. The main change in the voltage of capacitor C15 will be due to the loading effect of the input capacitance of the high voltage output switch 31 during switching on.

The snap-on, snap-off switch 204 is turned off when the oscillator signal is stopped and the voltage across capacitor C14 decays, due to the flow of current through resistor R14, to a voltage below the voltage threshold of transistor Q21. In this case transistors Q21, Q17 and Q19 will be turned off. The gate of transistor Q20 is then pulled down by the resistor R18, turning this transistor hard on, and thus clamping the voltage of the POS terminal, with respect to the NEG terminal, to the voltage threshold of transistor Q20, which is much less than the voltage required to turn on the MOSFET high voltage switch 31 (FIG. 3). Clamping the voltage across the output port 205 also protects the MOSFET high voltage switch against false switching that is due to high level system noise. This clamping function does not require any voltage across capacitors C14 or C15. Accordingly, the circuit protection against false switching is achieved even under idle conditions when the control circuit is not powered up.

The indirect drive control circuit 200 was simulation-tested by using it to drive a large output switch, configured as shown in FIG. 11, but utilizing an indirect drive control circuit 200 in place of the direct drive control circuit 100, and an oscillator signal of 5.6 V at 2 MHz. The tank capacitor 32 was charged to 750 V. The load resistors RL1 and RL2 were reduced to 10 ohms each. The peak load current in this circuit is 37.5 A. When the snap-on, snap-off switch 204 (FIG. 14) is turned on, it consumes a small current through the resistors R15 to R18. This is equivalent to connecting a resistive load of 417 K across capacitor C15. This forms an RC circuit with a time constant of 196 ms. Therefore, if the switch is left on for 20 ms, the voltage across capacitor C15 will only drop to 90% of its value as a result of the current through the above-mentioned resistors. The main change in the voltage of capacitor C15 will be due to the loading effect of the input capacitance of the high voltage output switch 31 during switching on.

Figure 15:
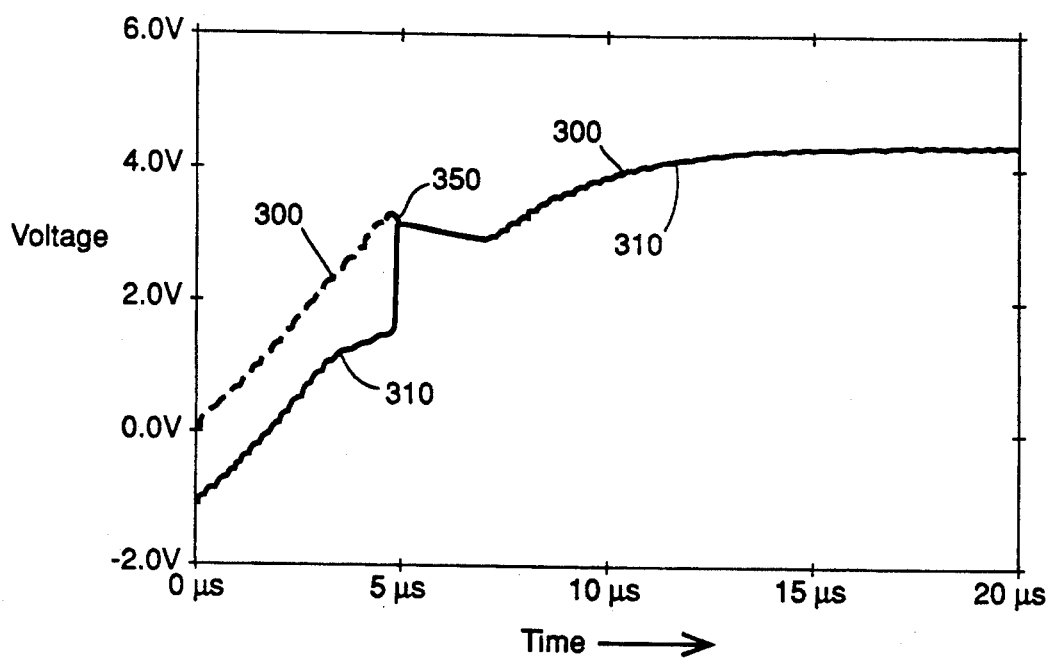
FIG. 15 shows the voltage across capacitor C14 of FIG. 14 during the turn on transient.

FIG. 15 shows, at 300, the voltage across the capacitor C14 for the first 20 $\mu$s after turning the oscillator signal on (i.e., the turn-on transient). The figure also shows, at 310, the gate-to-source voltage of the transistor Q21, where the effect of the positive hysteresis during switching is evident.

Figure 16:
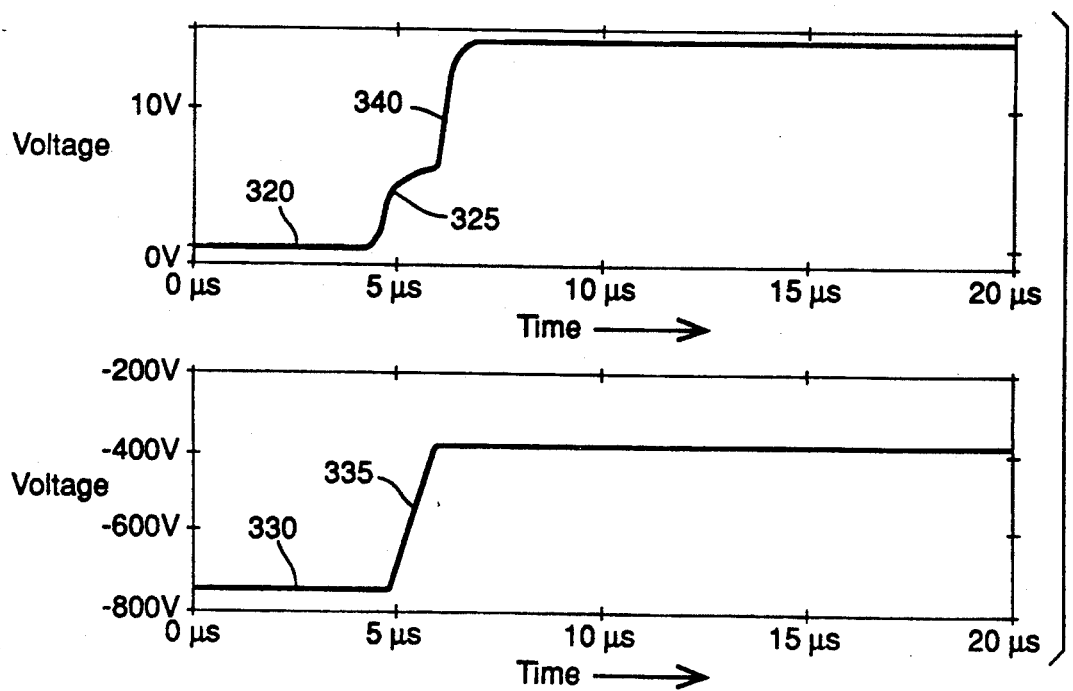
FIG. 16 shows the output voltage of a snap-on snap-off switch utilized in FIG. 14.

FIG. 16 shows, at 320, the output voltage of the snap-on, snap-off switch 204 when driving the gate of the high voltage MOSFET switch 31 (FIG. 11). It also shows, at 330, the common mode voltage of node 280 (FIG 14) with respect to the low voltage ground The common mode voltage changes from $-750$ V to $-375$ V in about 1.6 $\mu$s, as shown at 335. In spite of the high amplitude and fast rate of change of the common mode transients, they did not cause false turning off of the high voltage switch. A break 325 in the POS-to-NEG voltage curve 320 during switching 340 is due to the loading effect of the input capacitance of the high voltage switch 31. During this 1.6 $\mu$s rise time of the output pulse, the common mode transients were blocked by the common mode switch 31. As a result, the common mode switch stops charging the capacitor C14 and the voltage across this capacitor during this period drops slightly due to the discharging of capacitor C14 through resistor R14, as shown at 350 in curve 300 of FIG. 15.

Figure 17:
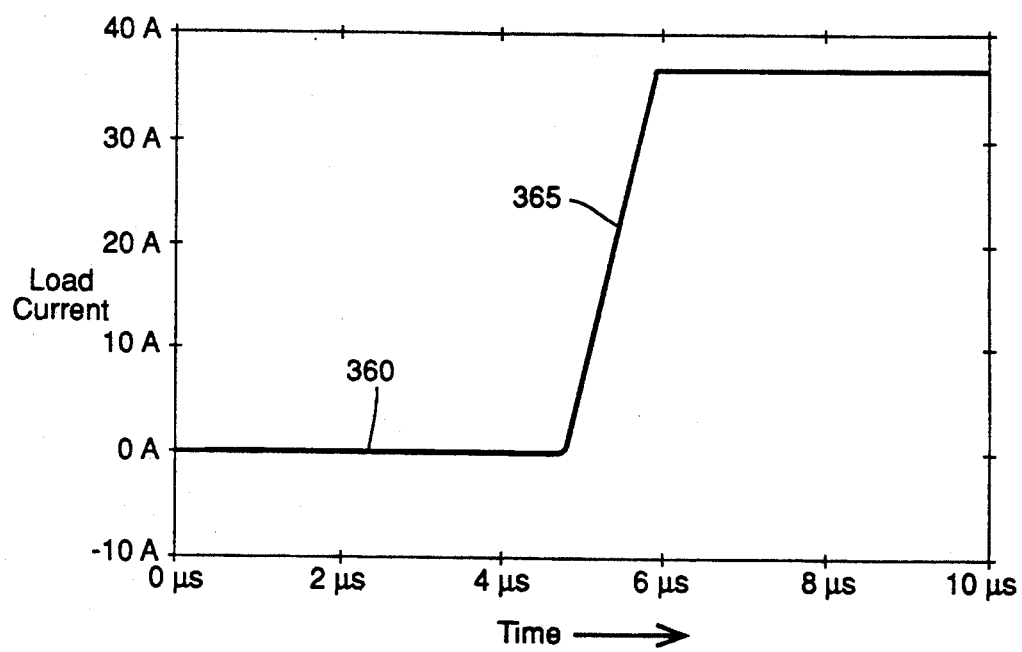
FIG. 17 is a graph showing the leading edge of a defibrillation current pulse developed in accordance with the present invention.

The leading edge of the load current (defibrillation current pulse) is shown at 360 in FIG. 17. It has a rise time (10% to 90% amplitude), shown at 365, of 1.45 $\mu$s.

Figure 18:
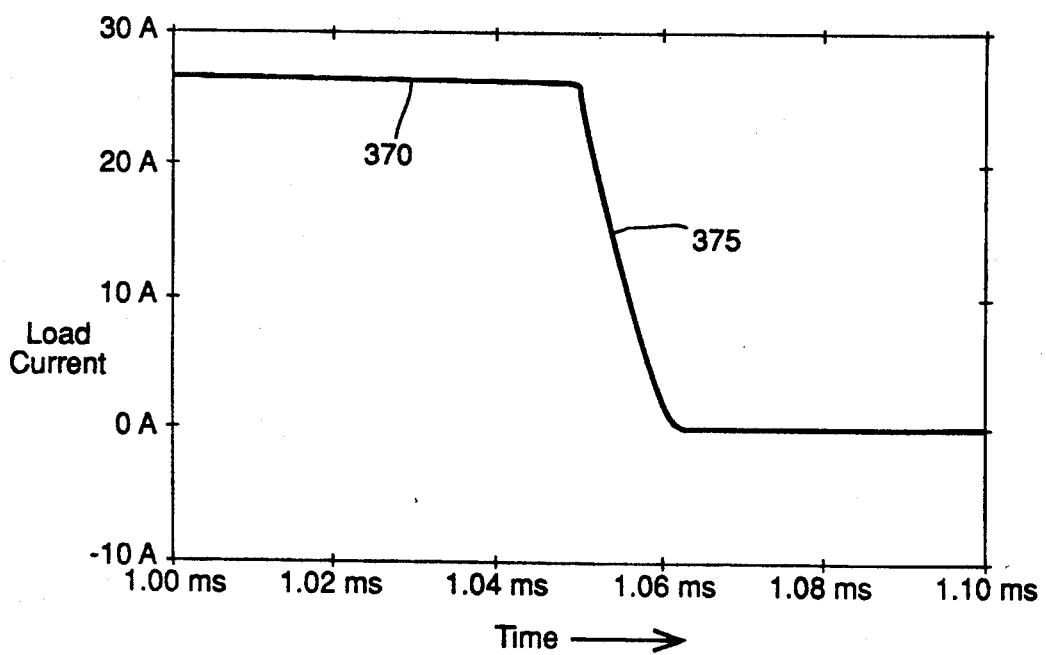
FIG. 18 is a graph showing the trailing edge of the defibrillation current pulse shown on FIG. 17.

FIG. 18 shows, at 370, the trailing edge of the load current (defibrillation current) pulse. This figure shows that the turn-off delay is about 50 $\mu$s and the turn-off time (from full amplitude to zero current), shown at 375, is 12 $\mu$s. The switching off of the output current is again bounce free and the common mode high voltage switching transients did not affect the performance of the circuit.

It will be apparent from the foregoing discussion that the present invention provides improved circuits for driving high voltage switches in implantable pacemaker/defibrillators and other medical devices by incorporating capacitive coupling techniques in place of the transformer coupling techniques used in similar prior art devices. Users of medical device incorporating the capacitive coupling techniques of the present invention benefit from the lower costs, reduced volume, greater functional reliability, lower susceptibility to the hazards of electromagnetic interference and lower power consumption of the devices. The circuitry of the invention allows the high voltage output switch of the device to be turned on and off in a very short time, preventing turn-on/turn-off transient currents from overheating and damaging the output switch. In addition the circuitry has a very high common mode rejection ratio, avoiding false switching of the high voltage output switch, and improving patient safety.

While there have been shown and described what are presently considered to be the preferred embodiment of this invention, it will be obvious to those skilled in the art that various changes and modifications may be made without departing from the broader aspects of this invention. It is, therefore, aimed in the appended claims to cover all such changes and modifications as fall within the true spirit and scope of this invention.

What is claimed is:

1. An implantable device for treating a malfunctioning heart, comprising:

high voltage circuit means including a tank capacitor for storing therein during a charging mode of operation thereof high voltage DC electrical energy and for delivering said energy to a malfunctioning heart in the form of an electrical shock during a discharging mode of operation thereof, and means for supplying high voltage electrical energy to said tank capacitor;

high voltage switch means coupled to said high voltage circuit means for switching, in the order of microseconds, said high voltage circuit means between said charging and discharging modes of operation;

power supply means for providing low voltage electrical energy for use in controlling said high voltage switch means;

control circuit means coupled between said power supply means and said high voltage switch means and capable of driving said high voltage switch means to switch its output in the order of microseconds, for controlling the operation of said high voltage switch means; and capacitor means for capacitively coupling said power supply means to said control circuit means and electrically isolating said high voltage DC electrical energy from said power supply means, said control circuit means including common mode switch means for rejecting common mode noise, and additional switch means for rapidly changing the output state of said high voltage switch means.

2. A device according to claim 1 wherein said power supply means includes an oscillator for providing oscillating low voltage energy to said control circuit means, and wherein said control circuit means includes rectifier means for converting said oscillating low voltage energy to a DC control voltage.

3. A device according to claim 2 wherein said rectifier means comprises a plurality of MOSFET transistors connected in a bridge circuit, and wherein said capacitor means capacitively couples said oscillator to said bridge circuit.

4. A device according to any one of claims 1-3, wherein said control circuit means includes a positive DC output voltage line and a negative DC output voltage line coupling said high voltage switch means to said control circuit means, and wherein said additional switch means for rapidly changing the output state of said high voltage switch means includes a capacitor connected between said positive and negative DC output voltage lines, a resistor connected between said positive and negative DC output voltage lines, a bipolar transistor having its emitter and base connected to said positive DC output voltage line at spaced apart points therein and its collector connected to said negative DC output voltage line, and a unidirectional conducting means connected in series in said positive DC output voltage line, intermediate the junctions of said base and emitter with said positive DC output voltage line, for preventing a reverse flow of current through said positive DC output voltage line.

5. A device according to any one of claims 1-3, wherein said control circuit means includes a positive DC control voltage line, a positive DC output voltage line and a negative DC voltage line therein, and wherein said additional switch means for rapidly changing the state of said high voltage switch means includes a first capacitor and a resistor each connected between said positive DC control voltage line and said negative DC voltage line, said first capacitor being charged by said low voltage electrical energy, a second capacitor, means for charging said second capacitor, and means responsive to the level of charge on said first capacitor and operative to couple said second capacitor across and decouple said second capacitor from said positive DC output voltage line and said negative DC voltage line for switching said high voltage switch means between said charging and discharging modes of operation.

6. A device according to claim 3, wherein said control circuit means includes a positive DC output voltage line and a negative DC output voltage line, and wherein said common mode switch means includes a first MOSFET transistor having a source and a drain connected in series with said positive DC output voltage line, a second MOSFET transistor having a source and a drain connected in series with said negative DC output voltage line, said first MOSFET transistor having a gate connected to said negative DC output voltage line downstream of said second MOSFET transistor, and said second MOSFET transistor having a gate connected to said positive DC output voltage line downstream of said first MOSFET transistor, said common mode switch means further including unidirectional conducting means connected in series in said positive DC output voltage line, intermediate said first MOSFET transistor and the junction of said gate of said second MOSFET transistor with said positive DC output voltage line, for preventing a reverse flow of current through said positive DC output voltage line.

7. A device according to claim 3, wherein said control circuit means includes a positive DC control voltage line, a positive DC output voltage line and a negative DC voltage line, and wherein said common mode switch means includes a first MOSFET transistor having a source and a drain connected in series with said positive DC control voltage line, a second MOSFET transistor having a source and a drain connected in series with said negative DC voltage line, said first MOSFET transistor having a gate connected to said negative DC voltage line downstream of said second MOSFET transistor, and said second MOSFET transistor having a gate connected to said positive DC control voltage line downstream of said first MOSFET transistor, said common mode switch means further including unidirectional conducting means connected in series in said positive DC control voltage line, intermediate said first MOSFET transistor and the junction of said gate of said second MOSFET transistor with said positive DC control voltage line, for preventing a reverse flow of current through said positive DC control voltage line.

8. A device according to claim 3, wherein said control circuit means includes a positive DC output voltage line and a negative DC output voltage line, and wherein said additional switch means for rapidly changing the output state of said high voltage switch means is positioned downstream of said common mode switch means and includes a capacitor connected between said positive and negative DC output voltage lines, a resistor connected between said positive and negative DC output voltage lines, a bipolar transistor having its emitter and base connected to said positive DC output voltage line at spaced apart points therein and its collector connected to said negative DC output voltage line, and a unidirectional conducting means connected in series in said positive DC output voltage line, intermediate the junctions of said base and emitter with said positive DC output voltage line, for preventing a reverse flow of current through said positive DC output line.

9. A device according to claim 8, wherein said common mode switch means includes a first MOSFET transistor having a source and a drain connected in series with said positive DC output voltage line, a second MOSFET transistor having a source and a drain connected in series with said negative DC output voltage line, said first MOSFET transistor having a gate connected to said negative DC output voltage line downstream of said second MOSFET transistor, and said second MOSFET transistor having a gate connected to said positive DC output voltage line downstream of said first MOSFET transistor, said common mode switch means further including unidirectional conducting means connected in series in said positive DC output voltage line, intermediate said first MOSFET transistor and the junction of said gate of said second MOSFET transistor with said positive DC output voltage line, for preventing a reverse flow of current through said positive DC output voltage line.

10. A device according to claim 3, wherein said control circuit means includes a positive DC control voltage line, a positive DC output voltage line, and a negative DC voltage line, and wherein said additional switch means for rapidly changing the output state of said high voltage switch means is positioned downstream of said common mode switch means and includes a first capacitor and a resistor each connected between said positive DC control voltage line and said negative DC voltage line, said first capacitor being charged by said low voltage electrical energy, a second capacitor, means for charging said second capacitor, and means responsive to the level of charge on said first capacitor and operative to couple said second capacitor across and decouple said second capacitor from said positive DC output voltage line and said negative DC voltage line for switching said high voltage switch means between said charging and discharging modes of operation.

11. A device according to claim 9, wherein said common mode switch means includes a first MOSFET transistor having a source and a drain connected in series with said positive DC control voltage line, a second MOSFET transistor having a source and a drain connected in series with said negative DC voltage line, said first MOSFET transistor having a gate connected to said negative DC voltage line downstream of said second MOSFET transistor, and said second MOSFET transistor having a gate connected to said positive DC control voltage line downstream of said first MOSFET transistor, said common mode switch means further including unidirectional conducting means connected in series in said positive DC control voltage line, intermediate said first MOSFET transistor and the junction of said gate of said second MOSFET transistor with said positive DC control voltage line, for preventing a reverse flow of current through said positive DC control voltage line.

12. A device according to any one of claims 6, 7, 10 or 11, wherein said bridge circuit of said rectifier includes first and second pairs of MOSFET transistors, each of said pairs being connected in a push-pull configuration in said bridge circuit, wherein said first MOSFET transistor includes a second gate connected to corresponding gates on each MOSFET transistor in said first pair of transistors and to one side of a biasing capacitor, and wherein said second MOSFET transistor includes a second gate connected to corresponding gates on each MOSFET transistor in said second pair of MOSFET transistors and to another side of said biasing capacitor.

13. A device according to claim 12, wherein said oscillator comprises a square wave generator.

14. A device according to any one of claims 2, 3, 6–10 and 11, wherein said oscillator comprises a square wave generator.

15. A device according to any one of claims 2, 3, 6–10 and 11, wherein said oscillator comprises a high frequency oscillator.

16. A device according to claim 12, wherein said oscillator comprises a high frequency oscillator.

* * * * *